United States Patent [19]

Santilli et al.

[11] Patent Number: 5,081,253

[45] Date of Patent: Jan. 14, 1992

[54] IMIDAZO(4,5-C)PYRIDINES AS ANTIOSTEOPOROTIC AGENTS

[75] Inventors: Arthur A. Santilli, Havertown; Anthony C. Scotese, King of Prussia; Donald P. Strike, St. Davids, all of Pa.

[73] Assignee: American Home Products Corporation, New York, N.Y.

[21] Appl. No.: 557,247

[22] Filed: Jul. 24, 1990

Related U.S. Application Data

[63] Continuation-in-part of Ser. No. 454,556, Dec. 21, 1989, abandoned.

[51] Int. Cl.$^5$ .................. C07D 471/02; A61K 31/395
[52] U.S. Cl. .................................................... 546/118
[58] Field of Search .......................... 546/118; 514/303

[56] References Cited

FOREIGN PATENT DOCUMENTS

| 0173552 | 3/1987 | Japan ................... 546/118 |
| 0003829 | 5/1989 | World Int. Prop. O. ........... 546/118 |
| 0003830 | 5/1989 | World Int. Prop. O. ........... 546/118 |
| 0003833 | 5/1989 | World Int. Prop. O. ........... 546/118 |

*Primary Examiner*—Mary C. Lee
*Assistant Examiner*—Jessica H. Nguyen
*Attorney, Agent, or Firm*—Walter Patton

[57] ABSTRACT

This invention relates to 2-substituted-imidazo[4,5-c]pyridines, to the process for their preparation, to pharmaceutical compositions containing said 2-substituted-imidazo[4,5-c]pyridines and to the use of said 2-substituted-imidazo[4,5-c]pyridines for modifying the balance between bone production and bone resorption in a host animal, including man.

35 Claims, No Drawings

IMIDAZO(4,5-C)PYRIDINES AS ANTIOSTEOPOROTIC AGENTS

This is a continuation-in-part application of copending application U.S. Ser. No. 07/454,556, filed Dec. 21, 1989, now abandoned.

This invention relates to 2-imidazo[4,5-c]pyridines, to the process for their preparation, to pharmaceutical compositions containing said 2-substituted-imidazo[4,5-c]pyridines and to the use of said 2-substituted-imidazo[4,5-c]pyridines for modifying the balance between bone production and bone resorption in a host animal, including man.

BACKGROUND OF THE INVENTION

Osteoporosis is a skeletal disorder which is evidenced by an increase in fracture incidence resulting from a decrease in bone density. In fact, both the bone mineral (calcium phosphate called "hydroxyapatite") and the bone matrix (major protein called "collagen") are lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the spine. At older ages, the brittleness of the bones becomes evident by the ease with which the proximal femur ("hip") fractures. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffereing from an osteoporotic condition, net bone resorption exceeds bone formation.

A survey indicates that in the United States there may be fifteen to twenty million people afflicted with osteoporosis [W. A. Peck (Chairman), NIH Osteoporosis Consensus Conference, J. Am. Med. Assoc., 10, 252:799-802 (1984)]. Various types of osteoporosis are designated according to special conditions believed to be causative: senile (aging); post-menopausal (female loss of estrogenesis); disuse (chronic immobilization); steroid (long term steroid treatment as in arthritis); hypercalcemia of malignancy. Osteoporosis may also be manifested in dental problems since the mandible appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorous, Vitamin D, calcium salts, fluorides and calcitonin.

Estrogen replacement therapy has been the therapy of choice for osteoporosis in post-menopausal women.

Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, overstrenuous excercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass in adults.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include phosphonates, calcitonin and mithramycin. However, all of these drugs suffer serious drawbacks.

Mithramycin, an antibiotic, has anti-tumor activity together with hypocalcemic activity, causing a reduction of serum calcium which in turn is believed to be indicative of a decrease in the relative rate of bone resorption—i.e., bone resorption relative to bone production. Side effects, however, include renal and hepatic toxicity as well as nausea. Likewise, the organic phosphonates have side effects which include extraskeletal calcification, hypotension and renal failure. Calcitonin presents an immunological problem because it is commonly derived from a non-human source. Thus, none of the foregoing agents are at present suitable for use alone in the treatment of osteoporosis.

PRIOR ART

The closest prior art is Japanese Patent J6 3146-883-A and International Patent Application WO 89/03829; WO 89/03830 and WO 89/03833.

SUMMARY OF THE INVENTION

This invention relates to novel 2-substituted-imidazo[4,5-c]pyridine derivatives useful in inhibiting bone resorption and having the formula (I) or its tautomer having the formula (I')

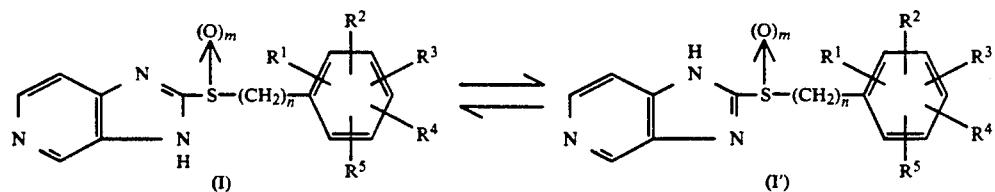

wherein $R^1$, $R^2$, $R^3$, $R^4$ and $R^5$ are independently selected from the group consisting of hydrogen, lower alkyl containing 1 to 6 carbon atoms, hydroxy, lower alkyloxy containing 1 to 6 carbon atoms, halogen, trifluoromethyl, trifluoromethoxy, nitro, cyano, phenoxy, benzyloxy, aminoacetyl, $-S(O)_p-CH_3$ or any two adjacent groups are joined to form methylenedioxy; m is 0 to 2; n is 1 to 3; p is 0 to 2, and the pharmaceutically acceptable salts and hydrates thereof.

Preferred compounds of the present invention are those of formula (I) wherein $R^1$, $R^2$, $R^3$, $R^4$ and $R^5$ are independently selected from the group consisting of hydrogen, hydroxy, methoxy, fluorine, chlorine, methyl, trifluoromethyl, benzyloxy or any two adjacent groups are joined to form methylenedioxy; m is 0 to 2; n is 1 to 2, and the pharmaceutically acceptable salts thereof.

The most preferred compounds of the present invention are designated

2-[[(3-methoxyphenyl)methyl]sulfinyl]-1H-imidazo[4,5-c]pyridine;
2-[[(3-methoxyphenyl)methyl]thio]-1H-imidazo[4,5-c]pyridine;
2-[[(3-methoxyphenyl)methyl]sulfonyl]-1H-imidazo[4,5-c]pyridine;
2-[[(3,4-dichlorophenyl)methyl]sulfinyl]-1H-imidazo[4,5-c]pyridine;
2-[[[3-(trifluoromethyl)phenyl]methyl]sulfinyl]-1H-imidazo[4,5-c]pyridine;
2-[[(2-chloro-6-fluorophenyl)methyl]sulfinyl]-1H-imidazo[4,5-c]pyridine;
2-[[(phenyl)methyl]sulfinyl]-1H-imidazo[4,5-c]pyridine;
2-[(2-phenylethyl)sulfinyl]-1H-imidazo[4,5-c]pyridine;
2-[[(3-methoxyphenyl)ethyl]sulfinyl]-1H-imidazo[4,5-c]pyridine;
2-[[(2,4,6-trimethylphenyl)methyl]sulfinyl]-1H-imidazo[4,5-c]pyridine;
2-[[(4-bromo-2-fluorophenyl)methyl]sulfinyl]-1H-imidazo[4,5-c]pyridine;
2-[[[3-(phenylmethoxy)phenyl]methyl]sulfinyl]-1H-imidazo[4,5-c]pyridine;
2-[[(6-chloro-1,3-benzodioxol-5-yl)methyl]sulfinyl]-1H-imidazo[4,5-c]pyridine;
2-[[(4-methoxyphenyl)methyl]sulfinyl]-1H-imidazo[4,5-c]pyridine;
2-[[(3,4,5-trimethoxyphenyl)methyl]sulfinyl]-1H-imidazo[4,5-c]pyridine;
2-[[(3,4-difluorophenyl)methyl]sulfinyl]-1H-imidazo[4,5-c]pyridine;
2-[[(pentafluorophenyl)methyl]sulfinyl]-1H-imidazo[4,5-c]pyridine;
2-[[(3-methylphenyl)methyl]sulfinyl]-1H-imidazo[4,5-c]pyridine;
2-[[(4-t-butylphenyl)methyl]sulfinyl]-1H-imidazo[4,5-c]pyridine;
2-[[(1H-imidazo[4,5-c]pyridin-2-yl)sulfinyl]methyl]benzonitrile;
2-[[(2-fluorophenyl)methyl]sulfinyl]-1H-imidazo[4,5-c]pyridine;
2-[[(2-methoxyphenyl)methyl]sulfinyl]-1H-imidazo[4,5-c]pyridine;
2-[[(3,5-dimethoxyphenyl)methyl]sulfinyl]-1H-imidazo[4,5-c]pyridine;
2-[[(3-phenoxyphenyl)methyl]sulfinyl]-1H-imidazo[4,5-c]pyridine;
2-[[(3-nitrophenyl)methyl]sulfinyl]-1H-imidazo[4,5-c]pyridine;
2-[[(4-methoxy-3-methylphenyl)methyl]sulfinyl]-1H-imidazo[4,5-c]pyridine;
2-[[(3-ethoxyphenyl)methyl]sulfinyl]-1H-imidazo[4,5-c]pyridine;
N-[4-[(1H-imidazo[4,5-c]pyridin-2-ylsulfinyl)methyl]phenyl]acetamide;
[S-(+)]-2-[[3-methoxyphenyl)methyl]sulfinyl]-1H-imidazo[4,5-c]pyridine;
[R-(−)]-2-[[(3-methoxyphenyl)methyl]sulfinyl]-1H-imidazo[4,5-c]pyridine;
3-[[(1H-imidazo[4,5-c]pyridin-2-yl)sulfinyl]methyl]phenol;

and the pharmaceutically acceptable salts thereof.

The sulfoxides of this invention possess an asymmetric sulfur atom and thus are made as racemic mixtures. It is to be understood that the definition of the sulfoxides of Formula (I) and (I') encompasses all possible stereoisomers, R and S enantiomers, tautomers and mixtures thereof which possess the activity discussed below. In particular, it encompasses racemic modifications and any optical isomers which possess the indicated activity.

It is another object of this invention to provide an improved process for the production of 2-substituted-imidazo[4,5-c]pyridines according to the following Reaction Scheme.

REACTION SCHEME

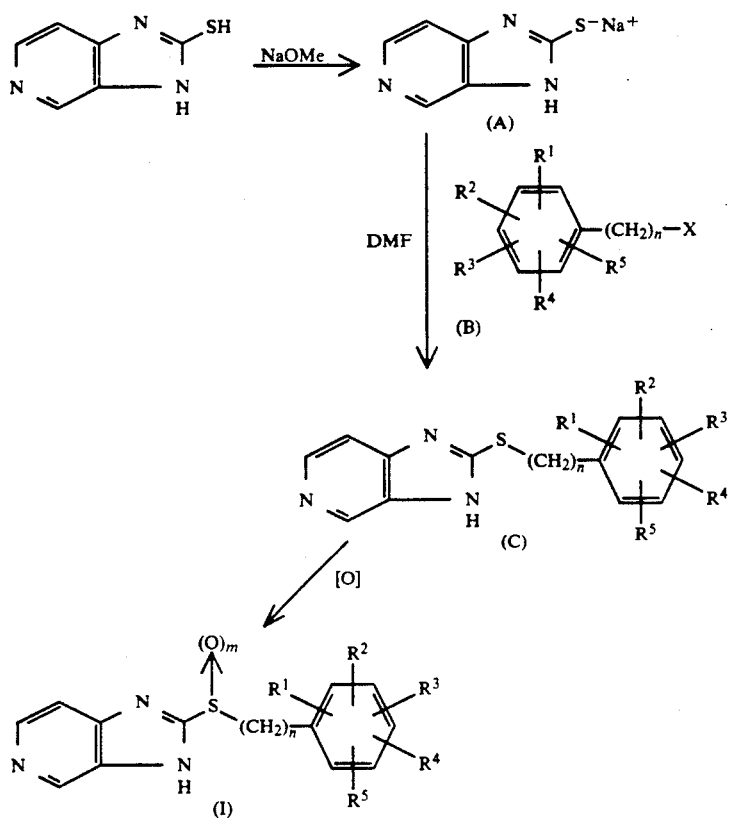

wherein $R^1, R^2, R^3, R^4, R^5$, m and n are as defined above and X is Cl, Br, I or tosyl.

The compounds of this invention are generally prepared sequentially by first forming the sodium salt of 2-mercaptoimidazo[4,5-c]pyridine (A) with sodium methoxide. Treatment of (A) in DMF with an equivalent of a suitably substituted alkylating agent (B), affords the corresponding sulfide derivative (C). Finally, oxidation of (C) with an equivalent of an oxidizing agent such as selenium dioxide/hydrogen peroxide or m-chloroperoxybenzoic acid at reduced temperature affords the desired sulfoxide (I).

It is also another object of this invention to provide a method whereby a host animal, including man, suffering from osteoporosis is treated in order to modify the balance between the rates of bone deposition and bone resorption in said host animal whereby the ratio of the latter to the former is reduced.

Still another object of this invention is to provide a process for the treatment of a host animal in order to prevent the deterioration of existing healthy bone tissues in said host animal. It is possible that these agents could also be of utility in the treatment of hypercalcemia of malignancy, Paget's disease, hyperparathyroidism, immobilization, glucocorticoid-induced osteopenia, and the arthritides.

It is a further object of this invention to provide a process for the treatment of periodontal disease.

DETAILED DESCRIPTION OF THE INVENTION

The compounds of formula (I) of this invention are used alone or in combination with pharmacologically acceptable carriers, the proportion of which is determined by the solubility and chemical nature of the compound, chosen route of administration and standard medical practice. For example, they are administered orally in the form of capsules, tablets, suspensions or solutions or by oral topical administration or they may be injected parenterally. Capsules and tablets are the preferred mode of administration. For parenteral administration they can be used in the form of a sterile solution containing other solutes, for example enough saline or glucose to make the solution isotonic.

The capsule and tablet compositions contain the active ingredient in admixture with non-toxic pharmaceutical excipients known to be suitable in the manufacture of capsules and tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula (I) contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula (I) will vary with the form of administration and the particular compound chosen. Furthermore, it will vary with the particular host as well as the age, weight and condition of the host under treatment, as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective amount of the compounds for oral administration can usually range from about 200 mg to 1200 mg/day in single or divided doses although, as aforementioned, variations will occur. However, a dosage level that is in the range of from about 500 mg to 900 mg/day in single or divided doses is employed most desirably for oral administration in order to achieve effective results.

The following examples are provided to illustrate the methods of preparation and testing of the compounds of the present invention. These examples are not meant to be considered, in any way, as limitations of the breadth and scope of the present invention. The temperatures expressed in these examples are in degrees centigrade.

EXAMPLE 1

2-Mercapto-1H-imidazo[4,5-c]pyridine

A mixture of 25 g (0.23 mol) of 3,4-diaminopyridine in 750 mL of ethanol containing 50 mL (63.2 g), 0.83 mol) of carbon disulfide was heated under reflux for 5 hours. The reaction mixture was allowed to cool to room temperature and the beige precipitate which had formed was collected by filtration and allowed to air dry overnight. The product amounted to 33.5 g, m.p. >320° C.

Ref. G. B. Barlin, J. Chem. Soc (B) 285 (1966).

EXAMPLE 2

2-[[(3-Methoxyphenyl)methyl]thio]-1H-imidazo[4,5-c]pyridine

To a solution containing 3.45 g (0.15 g atom) of sodium dissolved in 800 mL of methanol was added 22.65 g (0.15 mol) of 2-mercapto-1H-imidazo[4,5-c]pyridine. The reaction mixture was stirred for ½ hour at room temperature. The solvent was removed in a rotary evaporator and to the residue was added 465 mL of DMF. 3-Methoxybenzyl chloride (23.49 g, 0.15 mol) was then added dropwise and the reaction mixture was stirred overnight at room temperature. The reaction mixture was poured into approximately 1800 mL of water and allowed to cool for several hours in an ice bath. The product was removed by filtration and amounted to 28.3 g. Recrystallization from ethyl acetate gave 18.6 g of product. An analytical sample (m.p. 133°–136° C.) was obtained by recrystallization from ethanol.

Anal. Calcd. for $C_{14}H_{13}N_3OS$: C, 61.97; H, 4.83; N, 15.49. Found: C, 61.91; H, 4.81; N, 15.48.

EXAMPLE 3

2-[[(3-Methoxyphenyl)methyl]sulfinyl]-1H-imidazo[4,5-c]pyridine

2-[[(3-Methoxyphenyl)methyl]thio]-1H-imidazo[4,5-c]pyridine (9.88 g, 0.036 mol) was dissolved in 130 mL of methanol by heating. An oxidizing solution was prepared by dissolving 4.0 g (0.036 mol) of selenium dioxide in 150 mL of methanol with heating followed by the addition of 4.07 g (0.036 mol) of 30% hydrogen peroxide and 2.5 mL of water. The oxidizing solution was cooled to room temperature and was added dropwise to the sulfide solution. The reaction mixture was stirred overnight. The precipitate which had formed was collected on a filter and rinsed with petroleum ether giving 4.68 g of product. An analytical sample (m.p. 176°–179° C.) was obtained by recrystallization from ethanol.

Anal. Calcd. for $C_{14}H_{13}N_3O_2S$: C, 58.42; H, 4.56; N, 14.62. Found: C, 58.47; H, 4.53; N, 14.62.

EXAMPLE 4

2-[[3-Methoxyphenyl)methyl]sulfonyl]-1H-imidazo[4,5-c]pyridine

To a 2.35 g (0.009 mol) solution of 2-[[(3-methoxyphenyl)methyl]thio]-1H-imidazo[4,5-c]pyridine in 100 mL of methylene chloride was added, dropwise, and while stirring, a solution containing 4.2 g (0.02 mol) of m-chloroperoxybenzoic acid in 200 mL of methylene chloride. The reaction mixture was stirred at room temperature for four days. The precipitate (1.52 g) which formed was collected and washed with 10% sodium bicarbonate solution. An analytical sample (m.p. 200°–203° C.) was obtained by recrystallization from ethanol.

Anal. Calcd. for $C_{14}H_{13}N_3O_3S$: C, 55.43; H, 4.32; N, 13.85. Found: C, 55.66; H, 4.33; N, 13.98.

EXAMPLE 5

2-[[(3,4-Dichlorophenyl)methyl]thio]-1H-imidazo[4,5-c]pyridine

To a solution of 0.34 g (0.015 g atom) of sodium in 70 mL of methanol was added 2.0 g (0.013 mol) of 2-mercapto-1H-imidazo[4,5-c]pyridine. The reaction mixture was stirred at room temperature for 20 minutes and was evaporated to dryness in a rotary evaporator. To the residue was added 40 mL of DMF followed by the dropwise addition of 2.54 g (0.013 mol) of α,3,4-trichlorotoluene in 3 mL of DMF. The reaction mixture was stirred overnight at room temperature and was then poured into 400 mL of chilled water. The reaction mixture was extracted with chloroform (3×150 mL). The organic phases were combined and dried over magnesium sulfate. The solution was filtered and the filtrate was evaporated to dryness in a rotary evaporator. There was obtained 2.66 g of product. An analytical sample (m.p. 190°–193° C.) was obtained by recrystallization from acetonitrile.

Anal. Calcd. for $C_{13}H_9Cl_2N_3S$: C, 50.34; H, 2.92; N, 13.55. Found: C, 50.41; H, 2.72; N, 13.46.

EXAMPLE 6

2-[[(3,4-Dichlorophenyl)methyl]sulfinyl]-1H-imidazo[4,5-c]pyridine

[[(3,4-Dichlorophenyl)methyl]thio]-1H-imidazo[4,5-c]pyridine (1.3 g, 0.0042 mol) was dissolved in 26 mL of methanol with heating. An oxidizing solution consisting of 0.48 g (0.0042 mol) of selenium dioxide and 0.48 g (0.0042 mol) of 30% hydrogen peroxide and 0.5 mL of water in 9 mL of methanol was added dropwise to the sulfide solution. The reaction solution was stirred at room temperature overnight. The product (1.66 g) was collected by filtration. An analytical sample, m.p. 198°–201° C., was obtained by recrystallization from ethanol.

Anal. Calcd. for $C_{13}H_9Cl_2N_3OS$: C, 47.87; H, 2.78; N, 12.88. Found: C, 47.67; H, 2.77; N, 12.66.

EXAMPLE 7

2-[[[3-(Trifluoromethyl)phenyl]methyl]thio]-1H-imidazo[4,5-c]pyridine

To a solution of 0.15 g (0.0065 g atom) of sodium in 35 mL of methanol was added 1.0 g (0.0066 mol) of 2-mercapto-1H-imidazo[4,5-c]pyridine. After stirring for 15 minutes at room temperature, the methanol was removed in a rotary evaporator. The residue was dissolved in 20 mL of DMF and 1.28 g (0.0066 mol) of α'-chloro-α,α,α-trifluoro-m-xylene in 2 mL of DMF was added dropwise to the reaction solution. The reaction mixture was stirred at room temperature overnight and was then poured into 150 mL of ice water. The product which crystallized was collected and amounted to 1.61 g. An analytical sample (m.p. 148°–150° C.) was obtained by recrystallization from acetonitrile.

Anal. Calcd. for $C_{14}H_{10}F_3N_3S$: C, 54.36; H, 3.26; N, 13.59. Found: C, 54.45; H, 3.21; N, 13.50.

EXAMPLE 8

2-[[[3-(Trifluoromethyl)phenyl]methyl]-sulfinyl]-1H-imidazo[4,5-c]pyridine

2-[[[3-(Trifluoromethyl)phenyl]methyl]thio]-1H-imidazo[4,5-c]pyridine (0.91 g, 0.0029 mol) was dissolved in 10 mL of ethanol. An oxidizing solution was prepared by dissolving 0.32 g (0.0029 mol) of selenium dioxide in 17 mL of ethanol by heating and adding 0.33 g (0.0029 mol) of 30% hydrogen peroxide and 0.25 mL of water. The oxidizing solution was added dropwise to the sulfide solution and the reaction mixture was stirred overnight at room temperature. Water (20 mL) was added to the reaction mixture which was then extracted with chloroform (3×25 mL). The combined organic layers were dried over magnesium sulfate, filtered and evaporated to dryness. The residue amounted to 0.65 g. Purification by HPLC gave a product which on recrystallization from ethanol had a m.p. 194°–197° C.

Anal. Calcd. for $C_{14}H_{10}F_3OS$: C, 51.69; H, 3.10; N, 12.92. Found: C, 51.95; H, 3.07; N, 12.81.

EXAMPLE 9

2-[[(2-Chloro-6-fluorophenyl)methyl]thio]-1H-imidazo[4,5-c]pyridine

To a solution of 0.34 g (0.015 g atom) of sodium in 70 mL of ethanol was added 2.0 g (0.013 mol) of 2-mercapto-1H-imidazo[4,5-c]pyridine. After stirring at room temperature for 25 minutes, the reaction mixture was evaporated to dryness in a rotary evaporator. To the residue was added 40 mL of DMF. To the resulting solution was added dropwise 2.33 g (0.013 mol) of 2-chloro-6-fluorobenzyl chloride in 3 mL of DMF. The reaction mixture was stirred overnight at room temperature and was then poured into 400 mL of chilled water. The precipitate that formed was collected by filtration and amounted to 3.11 g. An analytical sample (m.p. 224°–226° C.) was obtained by recrystallization from ethanol.

Anal. Calcd. for $C_{13}H_9ClFN_3S$: C, 53.15; H, 3.09; N, 14.30. Found: C, 53.29; H, 3.30; N, 13.95.

EXAMPLE 10

2-[[(2-Chloro-6-fluorophenyl)methyl]-sulfinyl]-1H-imidazo[4,5-c]pyridine

2-[[(2-Chloro-6-fluorophenyl)methyl]thio]-1H-imidazo[4,5-c]pyridine (2.6 g, 0.0089 mol) was dissolved in 140 mL of methanol containing 20 mL of ethyl acetate. An oxidizing solution was prepared by heating 0.99 g (0.0089 mol) of selenium dioxide in 40 mL of methanol and adding 1.01 g (0.0089 mol) of 30% hydrogen peroxide and 0.65 mL of water. The oxidizing solution was added dropwise with stirring to the sulfide solution. The reaction mixture was stirred overnight at room temperature. Approximately ½ the solvent was removed in a rotary evaporator and the reaction mixture was chilled in ice. The resulting precipitate was collected and amounted to 1.08 g. An analytical sample, m.p. 180°–183° C., was obtained by recrystallization from ethanol.

Anal. Calcd. for $C_{13}H_9ClFN_3OS$: C, 50.41; H, 2.93; N, 13.57. Found: C, 50.45; H, 3.01; N, 13.26.

EXAMPLE 11

2-[[(Phenyl)methyl]thio]-1H-imidazo[4,5-c]pyridine

To a solution of 1.26 g (0.055 g atom) of sodium in 300 mL of methanol was added 7.56 g (0.05 mol) of 2-mercapto-1H-imidazo[4,5-c]pyridine with stirring. After 20 minutes, the reaction mixture was evaporated to dryness in a rotary evaporator. Dimethyl formamide (200 mL) was added to the residue. To the resulting solution was added dropwise 6.33 g (0.05 mol) of benzylchloride. The reaction mixture was stirred for 5 hours at room temperature and was then poured into 1500 mL of water. The product was removed by filtration and amounted to 9.5 g, m.p. 175°–177° C. The product was triturated with hot ethyl acetate and refiltered. The product amounted to 8.11 g, m.p. 175°–177° C. A portion recrystallized from ethyl acetate gave the analytical sample (m.p. 175°–177° C.).

Anal. Calcd. for $C_{13}H_{11}N_3S$: C, 64.70; H, 4.59; N, 17.41. Found: C, 64.55; H, 4.62; N, 17.12.

EXAMPLE 12

2-[[(Phenyl)methyl]sulfinyl]-1H-imidazo-[4,5-c]pyridine

To a chilled (0°–5° C.) solution of 3.3 g (0.014 mol) of 2-[[(phenyl)methyl]thio]-1H-imidazo[4,5-c]pyridine in 50 mL of chloroform and 5 mL of methanol was added dropwise a solution containing 2.78 g (0.014 mol) of m-chloroperoxybenzoic acid in 50 mL of chloroform. The reaction mixture was then stirred at room temperture for 45 minutes. Approximately one half of the chloroform was removed in a rotary evaporator and the reaction mixture was then poured into 200 mL of ether. The reaction mixture was cooled in ice. The precipitate that formed was collected and amounted to 1.78 g. The product was suspended in aqueous 10% sodium bicarbonate solution, filtered and was air dried overnight. The product amounted to 1.39 g. An analytical sample (m.p. 190°–193° C.) was obtained by recrystallization from ethanol.

Anal. Calcd. for $C_{13}H_{11}N_3OS$: C, 60.68; H, 4.31; N, 16.33. Found: C, 60.39; H, 4.17; N, 16.47.

EXAMPLE 13

2-[(2-Phenylethyl)thio]-1H-imidazo[4,5-c]pyridine

To a solution of 0.17 g (0.0074 g atom) of sodium in 35 mL of methanol was added 1.0 g (0.0066 mol) of 2-mercapto-1H-imidazo[4,5-c]pyridine. After stirring the reaction for 25 minutes at room temperature, the reaction mixture was evaporated to dryness in a rotary evaporator. To the residue was added 20 mL of DMF. To the resulting solution was added dropwise, 1.22 g (0.0066 mol) of 2-(bromoethyl)benzene in 3 mL of DMF. The reaction mixture was stirred overnight at room temperature and was then poured into 100 mL of chilled water. There was obtained 1.0 g of product. An analytical sample (m.p. 164°-166° C.) was prepared by recrystallization from ethanol.

Anal. Calcd. for $C_{14}H_{13}N_3S$: C, 65.85; H, 5.13; N, 16.46 Found: C, 66.04; H, 5.23; N, 16.06.

EXAMPLE 14

2-[(2-Phenylethyl)sulfinyl]-1H-imidazo[4,5-c]pyridine

2-[(2-Phenylethyl)thio]-1H-imidazo[4,5-c]pyridine (2.4 g, 0.0094 mol) was dissolved in 120 mL of chloroform with heating. The reaction solution was cooled in an ice bath to 0°-5° C. m-Chloroperoxybenzoic acid (1.91 g, 0.0094 mol) was added portionwise. The reaction mixture was then stirred at room temperature for 1 hour. 10% aqueous sodium bicarbonate was added and the organic layer was separated and dried over magnesium sulfate. After filtering, the filtrate was evaporated to half the volume in a rotary evaporator. Ether was added to the cloudy point and the reaction mixture was cooled in ice. The crystals that had formed amounted to 0.63 g. An analytical sample, m.p. 171°-174° C., was obtained by recrystallization from ethanol.

Anal. Calcd. for $C_{14}H_{13}N_3OS$: C, 61.97; H, 4.83; N, 15.49. Found: C, 61.73; H, 4.81; N, 15.09.

EXAMPLE 15

3-Methoxyphenethanol, p-Toluenesulfonate

A solution of 18.82 g (0.099 mol) of p-tosylchloride in 80 mL of pyridine was added dropwise to a solution of 12.5 g (0.082 mol) of 3-methoxyphenethyl alcohol in 120 mL of pyridine at ice bath temperature. The reaction mixture was then allowed to stir at room temperature for 2 hours. The pyridine was removed in a rotary evaporator. Water (100 mL) was added to the residue. The aqueous solution was then extracted with chloroform (3×100 mL). The combined chloroform layers were dried over magnesium sulfate, filtered and the filtrate taken to dryness in a rotary evaporator. The residual oil was purified by HPLC and used directly in the next step.

EXAMPLE 16

2-[[(3-Methoxyphenyl)ethyl]thio]-1H-imidazo[4,5-c]pyridine

To a solution of 0.81 g (0.035 g atom) of sodium in 170 mL of methanol was added 4.83 g (0.032 mol) of 2-mercapto-1H-imidazo[4,5-c]pyridine. After stirring for 25 minutes, the methanol was removed in a rotary evaporator and to the residue was added 100 mL of DMF. The residue dissolved after heating for a few minutes. The reaction mixture was allowed to cool to room temperature and 9.79 g (0.032 mol) of 3-methoxyphenethanol, p- toluenesulfonate ester in 5 mL of DMF was slowly added dropwise. The reaction mixture was allowed to stir at room temperature overnight and then was poured into 725 mL of chilled water. The reaction mixture was extracted with chloroform (3×200 mL). The combined organic phase was dried over magnesium sulfate, filtered and the filtrate was evaporated to dryness in a rotary evaporator. The crude product amounted to 12.6 g which was used directly in the next step.

EXAMPLE 17

2-[[(3-Methoxyphenyl)ethyl]sulfinyl]-1H-imidazo[4,5-c]pyridine

2-[[(3-Methoxyphenyl)ethyl]thio]-1H-imidazo[4,5-c]pyridine (4.0 g, 0.014 mol) was dissolved in 60 mL of chloroform and cooled in an ice bath to 0°-5° C. m-Chloroperoxybenzoic acid (3.13 g, 0.015 mol) was added in portions to the reaction mixture. After 45 minutes, 10% aqueous sodium bicarbonate solution was added. The organic layer was removed and dried over magnesium sulfate, filtered and evaporated to dryness in a rotary evaporator. The crude product (4.2 g) when subjected to HPLC gave 2.3 g of pure product, m.p. 125°-128° C.

Anal. Calcd. for $C_{15}H_{15}N_3O_2S$: C, 59.78; H, 5.02; N, 13.94. Found: C, 59.47; H, 4.84; N, 13.71.

EXAMPLE 18

2-[[(2,4,6-Trimethylphenyl)methyl]thio]-1H-imidazo[4,5-c]pyridine

The synthesis of this compound proceeded in the same fashion as in Example 11 using $\alpha^2$-chloroisodurene chloride, m.p. 150°-153° C.

Anal. Calcd. for $C_{16}H_{17}N_3S.4H_2O$: C, 66.75; H, 6.09; N, 14.59. Found: C, 66.84; H, 5.97; N, 14.67.

EXAMPLE 19

2-[[(2,4,6-Trimethylphenyl)methyl]sulfinyl]-1H-imidazo[4,5-c]pyridine

The synthesis of this compound proceeded in the same fashion as in Example 10, m.p. 214°-217° C.

Anal. Calcd. for $C_{16}H_{17}N_3OS$: C, 64.14; H, 5.72; N, 14.03. Found: C, 64.00; H, 5.66; N, 13.93.

EXAMPLE 20

2-[[(4-Bromo-2-fluorophenyl)methyl]thio]-1H-imidazo[4,5-c]pyridine

The synthesis of this compound proceeded in the same fashion as in Example 11 using 4-bromo-2-fluorobenzyl chloride, m.p. 204°-206° C.

Anal. Calcd. for $C_{13}H_9BrFN_3S$: C, 46.17; H, 2.68; N, 12.42. Found: C, 45.99; H, 2.81; N, 12.46.

EXAMPLE 21

2-[[(4-Bromo-2-fluorophenyl)methyl]sulfinyl]-1H-imidazo[4,5-c]pyridine

The synthesis of this compound proceeded in the same fashion as in Example 10, m.p. 208°-212° C. (dec.).

Anal. Calcd. for $C_{13}H_9BrFN_3OS$: C, 44.08; H, 2.56; N, 11.86. Found: C, 44.03; H, 2.59; N, 11.83.

EXAMPLE 22

2-[[[3-(Phenylmethoxy)phenyl]methyl]thio]-1H-imidazo[4,5-c]pyridine

The synthesis of this compound proceeded in the same fashion as in Example 11 using 3-benzyloxybenzyl chloride, m.p. 161°-164° C.

Anal. Calcd. for $C_{20}H_{17}N_3OS$: C, 69.14; H, 4.93; N, 12.09. Found: C, 68.90; H, 4.93; N, 11.59.

EXAMPLE 23

2-[[[3-(Phenylmethoxy)phenyl]sulfinyl]-1H-imidazo[4,5-c]pyridine

The synthesis of this compound proceeded in the same fashion as in Example 10, m.p. 195°-197° C. (dec.).

Anal. Calcd. for $C_{20}H_{17}N_3O_2S$: C, 66.09; H, 4.72; N, 11.56. Found: C, 65.93; H, 4.62; N, 11.54.

EXAMPLE 24

2-[[(6-Chloro-1,3-benzodioxol-5-yl)methyl]thio]-1H-imidazo[4,5-c]pyridine

The synthesis of this compound proceeded in the same fashion as in Example 11 using 6-chloropiperonyl chloride, m.p. 212°-214° C.

Anal. Calcd. for $C_{14}H_{10}ClN_3O_2S$: C, 52.59; H, 3.15; N, 13.14. Found: C, 52.52; H, 3.10; N, 12.77.

EXAMPLE 25

2-[[(2-Chloro-1,3-benzodioxol-5-yl)methyl]sulfinyl]-1H-imidazo[4,5-c]pyridine

The synthesis of this compound proceeded in the same fashion as in Example 10, m.p. 210°-213° C. (dec.).

Anal. Calcd. for $C_{14}H_{10}ClN_3O_3S$: C, 50.08; H, 3.00; N, 12.51. Found: C, 49.79; H, 2.94; N, 12.40.

EXAMPLE 26

2-[[(4-Methoxyphenyl)methyl]thio]-1H-imidazo[4,5-c]pyridine

The synthesis of this compound proceeded in the same fashion as in Example 11 using 4-methoxybenzyl chloride, m.p. 160°-161° C.

Anal. Calcd. for $C_{14}H_{13}N_3OS$: C, 61.97; H, 4.83; N, 15.49. Found: C, 62.00; H, 4.51; N, 15.22.

EXAMPLE 27

2-[[(4-Methoxyphenyl)methyl]sulfinyl]-1H-imidazo[4,5-c]-pyridine-One Third Hydrate The synthesis of this compound proceeded in the same fashion as in Example 10.

Anal. Calcd. for $C_{14}H_{13}N_3O_2S.\frac{1}{3} H_2O$: C, 57.32; H, 4.69; N, 14.32. Found: C, 57.31; H, 4.47; N, 14.12.

EXAMPLE 28

2-[[(3,4,5-Trimethoxyphenyl)methyl]thio]-1H-imidazo[4,5-c]pyridine Hydrochloride The synthesis of this compound proceeded in the same fashion as in Example 11. The product was characterized as the hydrochloride salt.

Anal. Calcd. for $C_{16}H_{18}ClN_3O_3S$: C, 52.24; H, 4.93; N, 11.42. Found: C, 52.28; H, 4.92; N, 11.29.

EXAMPLE 29

2-[[(3,4,5-Trimethoxyphenyl)methyl]sulfinyl]-1H-imidazo[4,5-c]pyridine-One Third Hydrate A solution of 5.56 g (0.009 mol) of magnesium monoperphthalate hexahydrate in 30 mL of water was added to 4.95 g (0.015 mol) of 2-[[(3,4,5-trimethylphenyl)methyl]thio]-1H-imidazo[4,5-c]pyridine (free base) in 50 mL of ethanol. The stirred reaction mixture was heated to 50° C. for 3 hours and then overnight at room temperature. An additional 1.86 g (0.003 mol) of the oxidant in 10 mL of water was added to the reaction mixture. The reaction mixture was heated for 1 hour at 50° C. An additional 30 mL of water was added and the reaction mixture was extracted with chloroform (3×40 mL). The combined organic phases were dried over $MgSO_4$, filtered and evaporated. The 5.4 g of residue was purified through HPLC and final recrystallization from EtOAc/MeOH to give 1.7 g of product, m.p. 118°-121° C.

Anal. Calcd. for $C_{16}H_{17}N_3O_4S.\frac{1}{3} H_2O$: C, 54.38; H, 5.04; N, 11.89. Found: C, 54.09; H, 5.03; N, 12.02.

EXAMPLE 30

2-[[(3,4-Difluorophenyl)methyl]thio]-1H-imidazo[4,5-c]pyridine

The synthesis of this compound proceeded in the same fashion as in Example 11 using α-bromo-3,4-difluorotoluene, m.p. 147°-149° C.

Anal. Calcd. for $C_{13}H_9F_2N_3S$: C, 56.31; H, 3.27; N, 15.15. Found: C, 56.00; H, 3.20; N, 14.96.

EXAMPLE 31

2-[[(3,4-Difluorophenyl)methyl]sulfinyl]-1H-imidazo[4,5-c]-pyridine-One Tenth Hydrate The synthesis of this compound proceeded in the same fashion as in Example 10, m.p. 170°-173° C. (dec.).

Anal. Calcd. for $C_{13}H_9F_2N_3OS.1/10 H_2O$: C, 52.91; H, 3.14; N, 14.24. Found: C, 52.75; H, 3.02; N, 14.18.

EXAMPLE 32

2-[[(Pentafluorophenyl)methyl]thio]-1H-imidazo[4,5-c]pyridine

The synthesis of this compound proceeded in the same fashion as in Example 11 using α-bromo-2,3,4,5,6-pentafluorotoluene, m.p. 156°-159° C.

Anal. Calcd. for $C_{13}H_6F_5N_3S$: C, 47.14; H, 1.83; N, 12.68. Found: C, 46.78; H, 1.52; N, 12.45.

EXAMPLE 33

2-[[(Pentafluorophenyl)methyl]sulfinyl]-1H-imidazo[4,5-c]pyridine-Hemihydrate

The synthesis of this compound proceeded in the same fashion as in Example 10, m.p. 114°-117° C.

Anal. Calcd. for $C_{13}H_6F_5N_3OS.\frac{1}{2} H_2O$: C, 43.82; H, 1.98; N, 11.79. Found: C, 43,65; H, 1.79; N, 11.78.

EXAMPLE 34

2-[[(3-Methylpheny)methyl]thio]-1H-imidazo[4,5-c]pyridine

The synthesis of this compound proceeded in the same fashion as in Example 11 using α-chloro-m-xylene, m.p. 166°-168° C.

Anal. Calcd. for $C_{14}H_{13}N_3S$: C, 65.85; H, 5.13; N, 16.46. Found: C, 65.64; H, 4.75; N, 16.37.

EXAMPLE 35

2-[[(3-Methylphenyl)methyl]sulfinyl]-1H-imidazo[4,5-c]pyridine-Quarter Hydrate The synthesis of this compound proceeded in the same fashion as in Example 10, m.p. 175°-177° C. (dec.).

Anal. Calcd. for $C_{14}H_{13}N_3OS \cdot \frac{1}{4} H_2O$: C, 60.96; H, 4.93; N, 15.23. Found: C, 60.93; H, 4.83; N, 15.11.

EXAMPLE 36

2-[[(4-t-Butylphenyl)methyl]thio]-1H-imidazo[4,5-c]pyridine

The synthesis of this compound proceeded in the same fashion as in Example 11 using 4-tert-butylbenzyl chloride, m.p. 207°-208° C.

Anal. Calcd. for $C_{17}H_{19}N_3S$: C, 68.65; H, 6.44; N, 14.13. Found: C, 68.43; H, 6.34; N, 14.11.

EXAMPLE 37

2-[[(4-t-Butylphenyl)methyl]sulfinyl]-1H-imidazo[4,5-c]pyridine

The synthesis of this compound proceeded in the same fashion as in Example 10, m.p. 215°-217° C. (dec.).

Anal. Calcd. for $C_{17}H_{19}N_3OS$: C, 65.15; H, 6.11; N, 13.40. Found: C, 64.67; H, 6.20; N, 13.07.

EXAMPLE 38

2-[(1H-Imidazo[4,5-c]pyridin-2-ylthio)methyl]benzonitrile

The synthesis of this compound proceeded in the same fashion as in Example 11 using α-bromo-o-tolunitrile, m.p. 200°-202° C.

Anal. Calcd. for $C_{14}H_{10}N_4S$: C, 63.14; H, 3.78; N, 21.04. Found: C, 62.87; H, 3.63; N, 20.83.

EXAMPLE 39

2-[[(1H-Imidazo[4,5-c]pyridin-2-yl)sulfinyl]methyl]benzonitrile

The synthesis of this compound proceeded in the same fashion as in Example 10, m.p. 179°-182° C.

Anal. Calcd. for $C_{14}H_{10}N_4OS$: C, 59.56; H, 3.57; N, 19.84. Found: C, 59.20; H, 3.38; N, 19.44.

EXAMPLE 40

2-[[(2-Fluorophenyl)methyl]thio]-1H-imidazo[4,5-c]pyridine

The synthesis of this compound proceeded in the same fashion as in Example 11 using 2-fluorobenzyl chloride, m.p. 186°-188° C.

Anal. Calcd. for $C_{13}H_{10}FN_3S$: C, 60.21; H, 3.89; N, 16.20. Found: C, 60.19; H, 3.76; N, 16.48.

EXAMPLE 41

2-[[(2-Fluorophenyl)methyl]sulfinyl]-1H-imidazo[4,5-c]pyridine Quarter Hydrate The synthesis of this compound proceeded in the same fashion as in Example 10, m.p. 145°-148° C. (dec.).

Anal. Calcd. for $C_{13}H_{10}FN_3OS \cdot \frac{1}{4}H_2O$: C, 55.80; H, 3.78; N, 15.02. Found: C, 55.77; H, 3.55; N, 14.94.

EXAMPLE 42

2-[[(2-Methoxyphenyl)methyl]thio]-1H-imidazo[4,5-c]pyridine

The synthesis of this compound proceeded in the same fashion as in Example 11 using 2-methoxybenzyl chloride, m.p. 193°-195° C.

Anal. Calcd. for $C_{14}H_{13}N_3OS$: C, 61.97; H, 4.83; N, 15.49. Found: C, 61.67; H, 5.00; N, 15.29.

EXAMPLE 43

2-[[(2-Methoxyphenyl)methyl]sulfinyl]-1H-imidazo[4,5-c]pyridine

The synthesis of this compound proceeded in the same fashion as in Example 10, m.p. 209°-211° C. (dec.).

Anal. Calcd. for $C_{14}H_{13}N_3O_2S$: C, 58.52; H, 4.56; N, 14.62. Found: C, 58.20; H, 4.57; N, 14.41.

EXAMPLE 44

2-[[(3,5-Dimethoxyphenyl)methyl]thio]-1H-imidazo[4,5-c]pyridine

The synthesis of this compound proceeded in the same fashion as in Example 11 using 3,5-dimethoxybenzyl chloride, m.p. 177°-179° C.

Anal. Calcd. for $C_{24}H_{25}N_3O_4S$: C, 63.85; H, 5.58; N, 9.31. Found: C, 63.60; H, 5.32; N, 9.15.

EXAMPLE 45

2-[[(3,5-Dimethoxyphenyl)methyl]sulfinyl]-1H-imidazo[4,5-c]pyridine

The synthesis of this compound proceeded in the same fashion as in Example 10, m.p. 207°-210° C. (dec.).

Anal. Calcd. for $C_{15}H_{15}N_3O_3S$: C, 56.77; H, 4.76; N, 13.24. Found: C, 56.53; H, 4.82; N, 12.89.

EXAMPLE 46

2-[[(3-Phenoxyphenyl)methyl]thio]-1H-imidazo[4,5-c]pyridine

The synthesis of this compound proceeded in the same fashion as in Example 11 using 3-phenoxybenzyl chloride, m.p. 156°-158° C.

Anal. Calcd. for $C_{19}H_{15}N_3OS$: C, 68.45; H, 4.53; N, 12.60. Found: C, 68.35; H, 4.44; N, 12.45.

EXAMPLE 47

2-[[(3-Phenoxyphenyl)methyl]sulfinyl]-1H-imidazo[4,5-c]pyridine

The synthesis of this compound proceeded in the same fashion as in Example 10, m.p. 210°-212° C. (dec.).

Anal. Calcd. for $C_{19}H_{15}N_3O_2S \cdot \frac{1}{4}H_2O$: C, 64.48; H, 4.42; N, 11.87. Found: C, 64.41; H, 4.18; N, 11.77.

EXAMPLE 48

2-[[(3-Nitrophenyl)methyl]thio]-1H-imidazo[4,5-c]pyridine

The synthesis of this compound proceeded in the same fashion as in Example 11 using 3-nitrobenzyl chloride, m.p. 208°-210° C.

Anal. Calcd. for $C_{13}H_{10}N_4O_2S$: C, 54.53; H, 3.52; N, 19.57. Found: C, 54.15; H, 3.70; N, 19.31.

EXAMPLE 49

2-[[(3-Nitrophenyl)methyl]sulfinyl]-1H-imidazo[4,5-c]pyridine 0.15 Dimethylformamide The synthesis of this compound proceeded in the same fashion as in Example 10, m.p. 214°–217° C. (dec.).

Anal. Calcd. for $C_{13}H_{10}N_4O_3S \cdot 0.15$ DMF: C, 51.56; H, 3.56; N, 18.56. Found: C, 51.48; H, 3.50; N, 18.50.

EXAMPLE 50

2-[[(4-Methoxy-3-methylphenyl)methyl]thio]-1H-imidazo[4,5-c]pyridine

The synthesis of this compound proceeded in the same fashion as in Example 11 using 4-methoxy-3-methylbenzyl chloride, m.p. 158°–159° C.

Anal. Calcd. for $C_{15}H_{15}N_3OS$: C, 63.13; H, 5.30; N, 14.73. Found: C, 62.95; H, 5.36; N, 14.67.

EXAMPLE 51

2-[[(4-Methoxy-3-methylphenyl)methyl]sulfinyl]-1H-imidazo[4,5-c]pyridine

The synthesis of this compound proceeded in the same fashion as in Example 10, m.p. 189°–192° C. (dec.).

Anal. Calcd. for $C_{15}H_{15}N_3O_2S$: C, 59.78; H, 5.02; N, 13.94. Found: C, 59.44; H, 4.70; N, 13.76.

EXAMPLE 52

2-[[(3-Ethoxyphenyl)methyl]thio]-1H-imidazo[4,5-c]pyridine

The synthesis of this compound proceeded in the same fashion as in Example 11 using 3-ethoxybenzyl chloride, m.p. 158°–161° C.

Anal. Calcd. for $C_{15}H_{15}N_3OS$: C, 63.13; H, 5.30; N, 14.72. Found: C, 62.98; H, 5.24; N, 14.47.

EXAMPLE 53

2-[[(3-Ethoxyphenyl)methyl]sulfinyl]-1H-imidazo[4,5-c]pyridine One Third Hydrate The synthesis of this compound proceeded in the same fashion as in Example 10, m.p. 166°–167° C. (dec.).

Anal. Calcd. for $C_{15}H_{15}N_3O_2S \cdot \frac{1}{3}H_2O$: C, 58.61; H, 5.14; N, 13.67. Found: C, 58.61; H, 4.89; N, 13.70.

EXAMPLE 54

3-[[(1H-Imidazo[4,5-c]pyridin-2-yl)thio]methyl]phenol Dihydrobromide

To 20 mL of boron trifluoride in a round bottom flask was added in portions and with stirring 2.49 g of 2-[[3-methoxyphenyl)methyl]thio]-1H-imidazo[4,5-c]pyridine (Example 2). The reaction flask was protected from moisture by a calcium chloride tube. Stirring was continued for 72 hours. The reaction mixture was added dropwise to 200 mL of methanol which was cooled in dry ice. The methanol solution was evaporated to one-half volume. The product which formed as a precipitate was collected on a filter and washed with acetone giving 1.07 g of white crystals, m.p. >300° C.

Anal. Calcd. for $C_{13}H_{11}N_3OS$: C, 37.25; H, 3.13; N, 10.02. Found: C, 36.86; H, 3.03; N, 10.40.

EXAMPLE 55

N-[4-[(1H-Imidazo[4,5-c]pyridin-2-ylthio)methyl]phenyl]acetamide

The synthesis of this compound proceeded in the same fashion as in Example 11 using 4-acetamidobenzyl chloride, m.p. 231°–234° C.

Anal. Calcd. for $C_{15}H_{14}N_4OS$: C, 60.38; H, 4.73; N, 18.78. Found: C, 60.28; H, 4.96; N, 18.42.

EXAMPLE 56

N-[4-[(1H-Imidazo[4,5-c]pyridin-2-ylsulfinyl)methyl]phenyl]acetamide One And One Quarter Hydrate The synthesis of this compound proceeded in the same fashion as in Example 12, m.p. 168°–171° C. (dec.).

Anal. Calcd. for $C_{15}H_{14}N_4O_2S \cdot 1.25 H_2O$: C, 53.71; H, 4.52; N, 16.70. Found: C, 53.77; H, 4.63; N, 16.06.

EXAMPLE 57

[S-(+)]-2-[[3-Methoxyphenyl)methyl]sulfinyl]-1H-imidazo[4,5-c]pyridine

A slurry of 6.0 g (0.0262 mol) of (+)-(2R, 8aS) (camphorylsulfonyl) oxaziridine in 125 mL of methylene chloride was sonicated at room temperature until a clear solution was obtained. A solution of 7.11 g (0.0262 mol) of 2-[[3-(methoxyphenyl)methyl]thio]-1H-imidazo[4,5-c]pyridine in 125 mL of ethanol was added to the oxaziridine solution. The reaction solution was sonicated for five days at 20° C., while running water through cooling coils. During the sonication process the reaction vessel was kept under a nitrogen atmosphere. The reaction mixture was subjected to HPLC. The fractions showing one spot corresponding to the desired sulfoxide were evaporated at room temperature. There was obtained 2.2 g of product $[\alpha]_D^{25} = +84.5°$. A chiral analytical HPLC column indicated the product was 81.3% (+) enantiomer and 18.7% (−) enantiomer, m.p. 185°–188° C. (dec.).

Anal. Calcd. for $C_{14}H_{13}N_3O_2S$: C, 58.52; H, 4.56; N, 14.62. Found: C, 58.14: H, 4.41; N, 14.51.

EXAMPLE 58

[R-(−)]-2-[[(3-Methoxyphenyl)methyl]sulfinyl]-1H-imidazo[4,5-c]pyridine One Quarter Hydrate Following the procedure of Example 57, the combined solutions of 5.16 g (0.019 mol) of 2-[[3-(methoxyphenyl)methyl]thio]-1H-imidazo[4,5-c]pyridine in 220 mL of ethanol and 7.15 g (0.019 mol) of (−)-α,α-dichlorocamphorsulfonyloxaziridine (F. A. Davis, R. T. Reddy, and M. C. Weismiller, J. Am. Chem. Soc., 111, 5964 (1989)) in 110 mL of methylene chloride were sonicated for 8 days at 20° C. The reaction mixture was subjected to HPLC. The fractions showing one spot corresponding to the desired sulfoxide were evaporated at room temperature. There was obtained 1.52 g of product, $[\alpha]_D^{25} = -99.4°$. A chiral analytical HPLC column indicated the product was 85.4% (−) enantiomer and 14.6% (+) enantiomer, m.p. 175°–178° C. (dec.).

Anal. Calcd. for $C_{14}H_{13}N_3O_2S \cdot \frac{1}{4}H_2O$: C, 57.62; H, 4.66; N, 14.40. Found: C, 57.69; H, 4.41; N, 14.30.

The useful osteoporotic activity of the compounds of formula (I) are demonstrated by standard pharmacological tests, for example, the test designated: *Bone Resorption Assay: $^{45}Ca$ Release from Rat Limb Bones*.

The purpose of this assay is to identify compounds that inhibit basal or stimulated bone resorption in culture.

The ability of 2-substituted-imidazo[4,5-c]pyridines to modify the process of bone resorption was evaluated essentially as described by L.G. Raisz, Bone resorption in tissue culture. Factors influencing the response to parathyroid hormone. (J. Clin. Invest. 44:103–116, 1965) and P. H. Stern et al, comparisons of fetal rat limb bones and neonatal mouse calvaria: Effects of parathyroid hormone and 1,25-dihydroxyvitamin $D_3$ (Calcif. Tissue Int. 35:172–176, 1983).

PROCEDURE

Limb Bone Preparation

Timed pregnant Sprague-Dawley CD® rats (Charles River) are administered 100 μCi $^{45}CaCl_2$ (NEN calcium −45 NEZ-013) in 100 μL of 0.9% saline, subcutaneously, on day 18 of gestation. The rats are sacrificed the following day by $CO_2$ asphyxiation. The fetuses are removed and the right forelimbs excised and placed in a Petri dish containing ice cold explant medium consisting of modified $BGJ_b$-Fitton Jackson media (custom formulation, Gibco No. 78-0088) adjusted to pH 7.3 to which 10 mM TES is added. The modified $BGJ_b$ media is obtained without salts, glucose or bicarbonate and is supplemented before use with 0.1 mM $MgCl_2$, 1.25 mM $CaCl_2$, 5.3 mM KCl, 0.7 mM $MgSO_4$, 130 mM NaCl, 1.0 mM $NaH_2PO_4$, 1 g/L glucose, 50 mg/L Na acetate and 100 U/mL penicillin G. The medium is sterilized by passage through a 0.2 μM filter (Nalge). Under a dissecting microscope, the bones are gently cleaned of adherent tissue and the cartilaginous ends removed. Incubation and drug treatment. The midshafts are placed, individually, on 3×3 mm squares of filter paper (Gelman GN-6 metricel filters; 0.45 μM pore size) which rest on stainless steel screens in wells of 24-well culture plates containing 0.5 mL of preincubation medium. The preincubation medium is brought to 37° C. prior to transfer of bones. The preincubation medium consists of the modified $BGJ_b$ medium (with salts and glucose as above), pH 7.3, containing 29 mM $NaHCO_3$. After incubation for 18-24 hours at 37° C. in 5% $CO_2$, the bones are transferred on their screen/filter paper supports to new plates containing, in a total volume of 0.5 mL/well at 37° C., the test compound diluted in preincubation medium supplemented with 15% heat inactivated horse serum (Gibco No. 230-6050), pH 7.3, with or without a bone resorption stimulating agent (e.g. parathyroid hormone [PTH] or interleukin-1 [IL-1]). For compounds that require nonaqueous solvents, dilutions are made from the appropriate stock solution with medium. In these instances, basal and bone resorption stimulated controls exposed to an equivalent concentration of the vehicle are included. An additional group of bones that have been subjected to boiling for 1 hour (kill control) are used to establish background, non cell mediated, exchange of $^{45}Ca$. The right ulna and radius from each fetus are used. Both bones are subjected to the same treatment and each treatment group consists of bones from 4 or more fetuses. Treatments are randomly assigned using a preclinical statistics program (PS-ALLOC). After a 48 hour incubation at 37° C. in 5% $CO_2$, the bones are removed from the medium and extracted in 0.5 mL of 0.1N HCl for 1 or more days. Duplicate 150 μL aliquots of the incubation medium and the bone extract are analyzed for $^{45}Ca$ radioactivity in 5 mL of liquid scintillation cocktail.

CALCULATIONS

The percentage of bone $^{45}Ca$ released into the medium is determined as follows:

$$\frac{^{45}Ca\ CPM\ in\ medium}{^{45}Ca\ CPM\ in\ medium + ^{45}Ca\ CPM\ in\ bone} \times 100$$

Results are normally expressed as the ratio of the percent $^{45}Ca$ release of the experimental group versus the appropriate vehicle control.

The results of this assay are set forth in TABLE 1 under the heading PTH Induced.

The useful osteoporotic activity of the compounds of formula (I) are further demonstrated by the test designated: Basal Bone Resorption Assay: $^{45}Ca$ Release from Rat Limb Bones.

The purpose of this assay is to test stimulators and inhibitors of bone resorption in vitro. The release of $^{45}Ca$ from in vitro labeled murine bone explants into the culture media is taken as an index of bone resorption.

Bone Labelling Procedure

Rat pups are labelled in vitro by injecting pregnant dams (18 days) with 100 μCi of $^{45}Ca$.

Explant Preparation

Two days after the initiation of labelling, the dam is anesthetized with halothane and killed by cervical dislocation. The pups are ablated and quickly decapitated. The calvaria (frontal and parietal bones), forelimbs (containing radii and ulnae), and hind limbs (tibiae) are removed and placed in control media in a petri dish. Bones are debrided of soft tissue by a combination of blunt dissection, and gentle rolling on bibulous paper, taking care not to disturb the periosteum. Cartilaginous ends are cut off long bones. Calvaria are cut in half along midline suture. Bones are separated into 3 categories: calvaria halves, Tibiae and ulnae/radii. Groups of eight (per bone group) are randomly placed in 24-well culture plates containing 0.5 mL of control media. Cultures are maintained at 37° C. in a humidified incubator of 95% air: 5% $CO_2$.

These bones are incubated for 24 hours, media is aspirated from the bones and replaced with fresh media containing test substances. Each bone group has a control group of 8 and a dead bone group of 8. The devitalized cultures are obtained by heating the bones in medium at 55° C. for 60 minutes. The bones are incubated at 37° C. for an additional 72 hours. At the end of this period a 100 microliter aliquot of media is removed and placed in a scintillation vial. Ten mL of Aquasol is added, the $^{45}Ca$ is quantified in a scintillation spectrometer. Bones are rinsed in saline, placed in a scintillation vial, hydrolyzed overnight in 0.75 mL 6N HCl at room temperature. The hydrolyzed bone solution is neutralized by the addition of 2.25 mL of 2N NaOH, followed by 10 mL of Aquasol, the $^{45}Ca$ content is determined by scintillation spectrometry.

Analysis: $^{45}Ca$ release into culture medium from the 24–96 hour period is individually compared to $^{45}Ca$ release in control cultures and to devitalized bone via Dunnett's test. Results are expressed in TABLE 1 under the heading Basal.

The useful osteoporotic activity of the compounds of formula (I) are further demonstrated by the test designated: *Denervation Induced Osteopenia in Rats.*

The purpose of this assay is to evaluate the effect, in rats, of agents on the reduction in bone mass (osteopenia) induced by immobilization resulting from surgical severance (denervation) of the sciatic nerve.

Female, Sprague Dawley CD ® rats, ovariectomized or intact, weighing 225 to 250 g, obtained from Charles River are used.

The animals are housed in plastic cages (4 or 5 rats/cage) with food (rat purina 500 chow) and water ad libitum; 14/10 day/night cycle.

After one week of in-house acclimatization, the animals are randomly divided into groups of 6 to 10 rats/group. Each rat is weighed, anesthetized with an intraperitoneal administration of 100 mg/kg ketamine (Bristol Laboratories, Syracuse, N.Y.) and 0.75 mg/kg Acepromazine (Aveco, Ft. Dodge, Iowa). The left hind limb is shaved and denervated by making a lateral incision parallel to the femur and by surgically removing half of a centimeter of the sciatic nerve adjacent to caudofemoralis and adductor brevis muscles. The incision is closed with wound clips. After surgery, the rats are housed in cages with absorbent bedding to minimize additional trauma to the immobilized limb. A 24 hour post-surgery recovery period is allowed before the initiation of the drug treatment.

The concentration of the drug stock is calculated to be delivered in a volume of 0.1 mL/100 gram body weight. The drug solution or a uniform suspension is prepared in 1% Tween 80 in normal saline. The drugs are administered via oral or parenteral routes daily (five times a week) for four weeks.

A sequential triple labeling of mineralized tissue is employed to determine the osseous changes (especially the bone formation) and the mineralization rates. Each animal is administered 90 mg/kg Xylenol orange (Fisher Scientific Company), S.C., 15 mg/kg Calcein (Sigma Chemical Company), S.C. and 15 mg/kg Demeclocycline (Sigma Chemical Company), i.p., approximately 21 days, 10 days and 2 days prior to the termination of the study, respectively.

At the end of the fourth week, each rat is weighed, anesthetized with an intraperitoneal administration of 100 mg/kg ketamine with 0.75 mg/kg Acepromazine and approximately 4 mL of blood collected via cardiac puncture. The anesthetized rats are euthanized by exposure to carbon dioxide. The femora and tibiae from both limbs are dissected free of soft tissue. (i) Femora are ashed at ~1100° C. for 16 hours using a muffle furnace. —(ii) Proximal tibia are fixed, dehydrated and embedded undecalcified in a methyl methacrylate-glycol methacrylate mixture. Longitudinal tissue sections (10 microns) are prepared on a Polycut S microtome (Reichert). Staining is performed on free-floating sections using a modified Goldner's stain, which are then mounted and coverslipped.

Cancellous bone content in the proximal tibia is quantified (as two dimensional bone mineral area [B.Ar]) with an image analysis processing device (software developed by Drexel University).

The areas of the tibia selected for cancellous bone content evaluation are the primary and secondary spongiosa. To select and standardize this area for evaluation, the epiphyseal growth plate-metaphyseal junction is oriented parallel to the abscissa of the digitizing screen. Bone elements 1.7 mm (secondary spongiosa) and 0.2 mm (primary spongiosa) from the growth plate and equidistant from the flanking cortical elements are then quantified as described above. The total area evaluated is 2.30 mm wide and 1.45 mm deep, constituting a 3.34 $mm^2$ area.

Body weight, femur mass (dried or ashed) and trabecular (cancellous) bone mineral area (B.Ar) are determined.

The difference (both absolute and percent change) in femur mass and bone mineral area between intact (control) and denervated limbs of a treatment group are compared with that for the vehicle group using a one-way analysis of variance with Dunnett's test, or other multiple comparison methods.

The results are reported in Table I and II under the heading In Vivo.

TABLE I

Imidazo[4,5-c]pyridine Sulfoxide and Sulfone Analogs

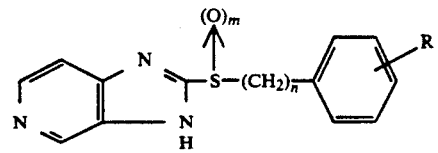

| Example | n | R | m | Inhibition of Bone Resorption | | |
|---|---|---|---|---|---|---|
| | | | | PTH Induced | Basal | In Vivo |
| 3 | 1 | 3-methoxy | 1 | Active $IC_{50}$ = 49 μM | Active 10 μg/mL | Active |
| 4 | 1 | 3-methoxy | 2 | Active 10 μg/mL | Marginal 10 μg/mL | Inactive |
| 6 | 1 | 3,4-dichloro | 1 | Active 10 μg/mL | Active 10 μg/mL | NT |
| 8 | 1 | 3-trifluoromethyl | 1 | Active 10 μg/mL | Inactive | NT |
| 10 | 1 | 2-chloro-6-fluoro | 1 | Active 10 μg/mL | Active 10 μg/mL | Inactive |
| 12 | 1 | hydrogen | 1 | Active 10 μg/mL | Active 10 μg/mL | Inactive |
| 14 | 2 | hydrogen | 1 | Active 10 μg/mL | Active 10 μg/mL | NT |
| 17 | 2 | 3-methoxy | 1 | Active 10 μg/mL | Inactive 10 μg/mL | Borderline |
| 19 | 1 | 2,4,6-trimethyl | 1 | Active 10 μg/mL | Active 10 μg/mL | Inactive |
| 21 | 1 | 2-fluoro-4-bromo | 1 | Active 10 μg/mL | Active 10 μg/mL | Inactive |
| 23 | 1 | 3-benzyloxy | 1 | Active 10 μg/mL | Active 10 μg/mL | Inactive |
| 25 | 1 | 2-chloro-4,5-methylenedioxy | 1 | Active 10 μg/mL | Active 10 μg/mL | Inactive |
| 27 | 1 | 4-methoxy | 1 | Active 10 μg/mL | NT | Inactive |
| 29 | 1 | 3,4,5-trimethoxy | 1 | Inactive | NT | Inactive |

TABLE I-continued

Imidazo[4,5-c]pyridine Sulfoxide and Sulfone Analogs

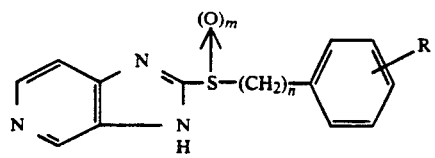

| | | | | Inhibition of Bone Resorption | | |
|---|---|---|---|---|---|---|
| Example | n | R | m | PTH Induced | Basal | In Vivo |
| 31 | 1 | 3,4-difluoro | 1 | Active 10 μg/mL | Active 10 μg/mL | Inactive |
| 33 | 1 | pentafluoro | 1 | NT | NT | NT |
| 35 | 1 | 3-methyl | 1 | NT | NT | NT |
| 37 | 1 | 4-tert-butyl | 1 | NT | NT | NT |
| 39 | 1 | 2-cyano | 1 | Active 10 μg/mL | NT | Inactive |
| 41 | 1 | 2-fluoro | 1 | Active 10 μg/mL | NT | Inactive |
| 43 | 1 | 2-methoxy | 1 | Active 10 μg/mL | NT | NT |
| 45 | 1 | 3,5-dimethoxy | 1 | Active 10 μg/mL | NT | Inactive |
| 47 | 1 | 3-phenoxy | 1 | Active 10 μg/mL | NT | Inactive |
| 49 | 1 | 3-nitro | 1 | NT | NT | Inactive |
| 51 | 1 | 4-methoxy-3-methyl | 1 | NT | NT | Inactive |
| 53 | 1 | 3-ethoxy | 1 | Active 10 μg/mL | NT | NT |
| 56 | 1 | 3-aminoacetyl | 1 | NT | NT | NT |
| 57 | 1 | S-(+)-3-methoxy | 1 | Active | NT | NT |
| 58 | 1 | R-(−)-3-methoxy | 1 | Active | NT | NT |

TABLE II

Imidazo[4,5-c]pyridine Sulfide Analogs

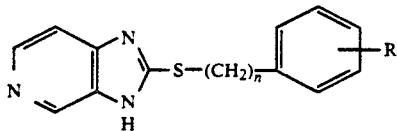

| | | | Inhibition of Bone Resorption | | |
|---|---|---|---|---|---|
| Example | n | R | PTH Induced 10 μg/mL | Basal 10 μg/mL | In Vivo 25 mg/kg |
| 2 | 1 | 3-methoxy | Inactive | Inactive | Active (i.p.) |
| 5 | 1 | 3,4-dichloro | NT | Inactive | NT |
| 7 | 1 | 3-trifluoromethyl | NT | Active | NT |
| 9 | 1 | 2-chloro-6-fluoro | Inactive | Inactive | NT |
| 11 | 1 | hydrogen | NT | Inactive | NT |
| 13 | 2 | hydrogen | Inactive | Inactive | NT |
| 16 | 2 | 3-methoxy | Inactive | NT | Inactive (p.o.) |
| 18 | 1 | 2,4,6-trimethyl | NT | NT | NT |
| 20 | 1 | 2-fluoro-4-bromo | Active | Inactive | NT |
| 22 | 1 | 3-benzyloxy | Active | Inactive | NT |
| 24 | 1 | 2-chloro-4,5-methylenedioxy | Active | NT | NT |
| 26 | 1 | 4-methoxy | Active | Inactive | Inactive (p.o.) |
| 28 | 1 | 3,4,5-trimethoxy | NT | NT | NT |
| 30 | 1 | 3,4-difluoro | Inactive | Inactive | Inactive (p.o.) |
| 32 | 1 | pentafluoro | Inactive | Inactive | Inactive (p.o.) |
| 34 | 1 | 3-methyl | NT | NT | NT |
| 36 | 1 | 4-tert-butyl | NT | NT | NT |
| 38 | 1 | 2-cyano | Inactive | NT | Inactive |
| 40 | 1 | 2-fluoro | Active | NT | Inactive |
| 42 | 1 | 2-methoxy | Active | NT | NT |
| 44 | 1 | 3,5-dimethoxy | Active | NT | Inactive |
| 46 | 1 | 3-phenoxy | Inactive | NT | Inactive |
| 48 | 1 | 3-nitro | NT | NT | Inactive |
| 50 | 1 | 4-methoxy-3-methyl | NT | NT | Inactive |
| 52 | 1 | 3-ethoxy | Inactive | NT | Inactive |
| 54 | 1 | 3-hydroxy | Inactive | NT | Inactive |
| 55 | 1 | 3-aminoacetyl | NT | NT | NT |

Bone is degraded during the process of bone resorption and this leads to the subsequent development of osteoporosis. The present invention provides a method for the treatment of a host animal in order to modify the balance between the rate of bone resorption and the rate of bone deposition in said host animal whereby the ratio of said rate of bone resorption to said rate of bone deposition is reduced, comprising administering to said host animal an amount, sufficient to modify said balance and reduce said ratio, of 2-substituted-imidazo[4,5-c]pyridines. 2Substituted-imidazo[4,5-c]pyridines would be administered to humans at a daily dose of 200 mg to 1200 mg.

The administration of 2-substituted-imidazo[4,5-c]pyridines in accordance with this invention can be supplemental to other regimens for the treatment of osteoporosis or periodontitis. For example, the administration of 2-substituted-imidazo[4,5-c]pyridines can be supplemental to the 600 mg to 1200 mg daily intake of calcium as calcium phosphate or calcium carbonate. Also, the administration of 2-substituted-imidazo[4,5-c]pyridines can be supplemental to estrogen replacement therapy such as 0.625 mg daily of conjugated equine estrogen.

We claim:

1. The compounds of formula (I)

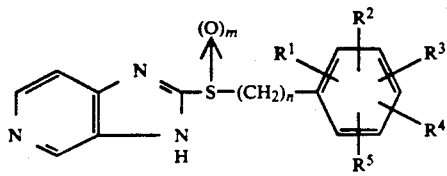

wherein $R^1$, $R^2$, $R^3$, $R^4$ and $R^5$ are independently selected from the group consisting of hydrogen, lower alkyl containing 1 to 6 carbon atoms, hydroxy, lower alkyloxy containing 1 to 6 carbon atoms, halogen, trifluoromethyl, trifluoromethoxy, nitro, cyano, phenoxy, benzyloxy, aminoacetyl, $—S(O)_p—CH_3$ or any two adjacent groups are joined to form methylenedioxy; m is 0 to 2; n is 1 to 3; p is 0 to 2, and the pharmaceutically acceptable salts and hydrates thereof.

2. The compounds according to claim 1 of formula (I) wherein $R^1$, $R^2$, $R^3$, $R^4$ and $R^5$ are independently selected from the group consisting of hydrogen, hydroxy, methoxy, fluorine, bromine, chlorine, methyl, trifluoromethyl, benzyloxy or any two adjacent groups are joined to form methylenedioxy; m is 0 to 2; n is 1 to 2, and the pharmaceutically acceptable salts thereof.

3. The compound according to claim 2 which is 2-[[(3-methoxyphenyl)methyl]sulfinyl]-1H-imidazo[4,5-c]pyridine and the pharmaceutically acceptable salts thereof.

4. The compound according to claim 2 which is 2-[[(3-methoxyphenyl)methyl]thio]-1H-imidazo[4,5-c]pyridine and the pharmaceutically acceptable salts thereof.

5. The compound according to claim 2 which is 2-[[(3-methoxyphenyl)methyl]sulfonyl]-1H-imidazo[4,5-c]pyridine and the pharmaceutically acceptable salts thereof.

6. The compound according to claim 2 which is 2-[[(3,4-dichlorophenyl)methyl]sulfinyl]-1H-imidazo[4,5-c]pyridine and the pharmaceutically acceptable salts thereof.

7. The compound according to claim 2 which is 2-[[[3-trifluoromethyl)phenyl]methyl]sulfinyl]-1H-imidazo[4,5-c]pyridine and the pharmaceutically acceptable salts thereof.

8. The compound according to claim 2 which is 2-[[(2-chloro-6-fluorophenyl)methyl]sulfinyl]-1H-imidazo[4,5-c]pyridine and the pharmaceutically acceptable salts thereof.

9. The compound according to claim 2 which is 2-[[(phenyl)methyl]sulfinyl]-1H-imidazo[4,5-c]pyridine and the pharmaceutically acceptable salts thereof.

10. The compound according to claim 2 which is 2-[(2-phenylethyl)sulfinyl]-1H-imidazo[4,5-c]pyridine and the pharmaceutically acceptable salts thereof.

11. The compound according to claim 2 which is 2-[[(3-methoxyphenyl)ethyl]sulfinyl]-1H-imidazo[4,5-c]pyridine and the pharmaceutically acceptable salts thereof.

12. The compound according to claim 2 which is 2-[[(2,4,6-trimethylphenyl)methyl]sulfinyl]-1H-imidazo[4,5-c]pyridine and the pharmaceutically acceptable salts thereof.

13. The compound according to claim 2 which is 2-[[(4-bromo-2-fluorophenyl)methyl]sulfinyl]-1H-imidazo[4,5-c]pyridine and the pharmaceutically acceptable salts thereof.

14. The compound according to claim 2 which is 2-[[[3-(phenylmethoxy)phenyl]methyl]sulfinyl]-1H-imidazo[4,5-c]pyridine and the pharmaceutically acceptable salts thereof.

15. The compound according to claim 2 which is 2-[[(6-chloro-1,3-benzodioxol-5-yl)methyl]sulfinyl]-1H-imidazo[4,5-c]pyridine and the pharmaceutically acceptable salts thereof.

16. The compound according to claim 2 which is 2-[[(4-methoxyphenyl)methyl]sulfinyl]-1H-imidazo[4,5-c]pyridine and the pharmaceutically acceptable salts thereof.

17. The compound according to claim 2 which is 2-[[(3,4,5-trimethoxyphenyl)methyl]sulfinyl]-1H-imidazo[4,5-c]pyridine and the pharmaceutically acceptable salts thereof.

18. The compound according to claim 2 which is 2-[[3,4-difluorophenyl)methyl]sulfinyl]-1H-imidazo[4,5-c]pyridine and the pharmaceutically acceptable salts thereof.

19. The compound according to claim 2 which is 2-[[(pentafluorophenyl)methyl]sulfinyl]-1H-imidazo[4,5-c]pyridine and the pharmaceutically acceptable salts thereof.

20. The compound according to claim 2 which is 2-[[(3-methylphenyl)methyl]sulfinyl]-1H-imidazo[4,5-c]pyridine and the pharmaceutically acceptable salts thereof.

21. The compound according to claim 2 which is 2-[[(4-t-butylphenyl)methyl]sulfinyl]-1H-imidazo[4,5-c]pyridine and the pharmaceutically acceptable salts thereof.

22. The compound according to claim 2 which is 2-[[(1H-imidazo[4,5-c]pyridin-2-yl)sulfinyl]methyl]benzonitrile and the pharmaceutically acceptable salts thereof.

23. The compound according to claim 2 which is 2-[[(2-fluorophenyl)methyl]sulfinyl]-1H-imidazo[4,5-c]pyridine and the pharmaceutically acceptable salts thereof.

24. The compound according to claim 2 which is 2-[[(2-methoxyphenyl)methyl]sulfinyl]-1H-imidazo[4,5-c]pyridine and the pharmaceutically acceptable salts thereof.

25. The compound according to claim 2 which is 2-[[(3,5-dimethoxyphenyl)methyl]sulfinyl]-1H-imidazo[4,5-c]pyridine and the pharmaceutically acceptable salts thereof.

26. The compound according to claim 2 which is 2-[[(3-phenoxyphenyl)methyl]sulfinyl]-1H-imidazo[4,5-c]pyridine and the pharmaceutically acceptable salts thereof.

27. The compound according to claim 2 which is 2-[[(3-nitrophenyl)methyl]sulfinyl]-1H-imidazo[4,5-c]pyridine and the pharmaceutically acceptable salts thereof.

28. The compound according to claim 2 which is 2-[[(4-methoxy-3-methylphenyl)methyl]sulfinyl]-1H-imidazo[4,5-c]pyridine and the pharmaceutically acceptable salts thereof.

29. The compound according to claim 2 which is 2-[[(3-ethoxyphenyl)methyl]sulfinyl]-1H-imidazo[4,5-c]pyridine and the pharmaceutically acceptable salts thereof.

30. The compound according to claim 2 which is N-[4-[(1H-imidazo[4,5-c]pyridin-2-ylsulfinyl)methyl]phenyl]acetamide and the pharmaceutically acceptable salts thereof.

31. The compound according to claim 2 which is [S-(+)]-2-[[3-methoxyphenyl)methyl]sulfinyl]-1H-imidazo[4,5-c]pyridine and the pharmaceutically acceptable salts thereof.

32. The compound according to claim 2 which is [R-(−)]-2-[[(3-methoxyphenyl)methyl]sulfinyl]-1H-imidazo[4,5-c]pyridine and the pharmaceutically acceptable salts thereof.

33. The compound according to claim 2 which is 3-[[(1H-imidazo[4,5-c]pyridin-2-yl)sulfinyl]methyl]phenol and the pharmaceutically acceptable salts thereof.

34. A pharmaceutical composition useful for modifying the balance between the rate of bone resorption and the rate of bone formation in a host animal whereby the ratio of said rate of bone resorption to said rate of bone formation is reduced, comprising a compound of formula (I) and a pharmaceutically acceptable carrier.

35. A method for the treatment of a host animal in order to modify the balance between the rate of bone resorption and the rate of bone formation in said host animal whereby the ratio of said rate of bone resorption to said rate of bone formation is reduced, comprising administering to said host animal an amount of a compound of formula (I) sufficient to modify said balance and reduce said ratio.

* * * * *